(12) United States Patent
Liu et al.

(10) Patent No.: US 9,835,609 B2
(45) Date of Patent: Dec. 5, 2017

(54) SYSTEM AND METHOD FOR DETERMINING FLUID VISCOSITY OF A FLUID IN A ROCK FORMATION

(71) Applicant: Chevron U.S.A. Inc., San Ramon, CA (US)

(72) Inventors: Chengbing Liu, Katy, TX (US); Stephen Newton, Berkshire (GB)

(73) Assignee: CHEVRON U.S.A. INC., San Ramon, CA (US)

( * ) Notice: Subject to any disclaimer, the term of this patent is extended or adjusted under 35 U.S.C. 154(b) by 326 days.

(21) Appl. No.: 14/668,361

(22) Filed: Mar. 25, 2015

(65) Prior Publication Data

US 2016/0282322 A1 Sep. 29, 2016

(51) Int. Cl.
*E21B 49/08* (2006.01)
*G01N 33/28* (2006.01)
*E21B 47/10* (2012.01)
*G01N 11/02* (2006.01)
*G01N 11/00* (2006.01)

(52) U.S. Cl.
CPC ......... *G01N 33/2823* (2013.01); *E21B 47/10* (2013.01); *E21B 49/08* (2013.01); *G01N 11/02* (2013.01); *E21B 2049/085* (2013.01); *G01N 2011/0073* (2013.01)

(58) Field of Classification Search
CPC ................. E21B 2049/085; G01B 2011/0073
See application file for complete search history.

(56) References Cited

U.S. PATENT DOCUMENTS

| 4,813,028 | A | * | 3/1989 | Liu | G01V 1/46 367/25 |
| 4,831,600 | A | * | 5/1989 | Hornby | G01V 1/50 367/31 |
| 4,881,208 | A | * | 11/1989 | Liu | G01V 1/46 181/105 |
| 5,616,840 | A | * | 4/1997 | Tang | E21B 49/00 367/31 |
| 5,687,138 | A | | 11/1997 | Kimball et al. | |
| 5,999,484 | A | * | 12/1999 | Kimball | G01V 1/50 367/31 |
| 6,727,696 | B2 | * | 4/2004 | Kruspe | E21B 33/1243 324/303 |
| 6,854,338 | B2 | * | 2/2005 | Khuri-Yakub | B01F 11/0258 1/258 |
| 6,933,719 | B2 | * | 8/2005 | Thomann | G01V 3/32 324/303 |

(Continued)

OTHER PUBLICATIONS

Brie, Quantitative Formation Permeability Evaluation from Stoneley Waves, SPE49131, Sep. 1998.

*Primary Examiner* — John Fitzgerald
(74) *Attorney, Agent, or Firm* — Karen R. DiDomenicis

(57) ABSTRACT

A system and a method are provided for determining a viscosity of a fluid in a rock formation. The method includes determining a Stoneley mobility using a Stoneley wave measurement in a rock formation containing a fluid; determining a wireline formation tester (WFT) downhole fluid analysis (DFA) mobility by using a wireline formation tester in the rock formation; and determining a viscosity of the fluid based on the Stoneley mobility and the wireline formation tester (WFT) downhole fluid analysis (DFA) mobility.

10 Claims, 5 Drawing Sheets

(56) References Cited

U.S. PATENT DOCUMENTS

| | | | |
|---|---|---|---|
| 7,193,414 B2* | 3/2007 | Kruspe | E21B 33/1243 324/303 |
| 7,257,490 B2* | 8/2007 | Georgi | G01V 11/00 702/11 |
| 7,310,580 B2 | 12/2007 | Zhou et al. | |
| 7,356,413 B2* | 4/2008 | Georgi | G01N 24/081 702/11 |
| 7,363,161 B2* | 4/2008 | Georgi | G01N 24/081 324/303 |
| 7,652,950 B2 | 1/2010 | Sinha et al. | |
| 7,825,659 B2* | 11/2010 | Georgi | G01N 24/081 324/303 |
| 7,830,744 B2 | 11/2010 | Wu et al. | |
| 7,894,300 B2 | 2/2011 | Hawthorn et al. | |
| 7,970,544 B2 | 6/2011 | Tang et al. | |
| 8,553,493 B2 | 10/2013 | Wu et al. | |
| 8,607,628 B2* | 12/2013 | Charara | G01V 1/50 73/152.01 |
| 8,682,587 B2 | 3/2014 | Singer et al. | |
| 9,013,954 B2* | 4/2015 | Parshin | G01V 11/00 367/28 |
| 9,477,002 B2* | 10/2016 | Miller | E21B 33/124 |
| 2002/0083771 A1* | 7/2002 | Khuri-Yakub | B01F 11/0258 1/258 |
| 2002/0153888 A1* | 10/2002 | Kruspe | E21B 33/1243 324/303 |
| 2005/0007109 A1* | 1/2005 | Thomann | G01V 3/32 324/303 |
| 2006/0273788 A1* | 12/2006 | Georgi | G01V 3/32 324/303 |
| 2006/0276969 A1* | 12/2006 | Georgi | G01V 11/00 702/11 |
| 2006/0285437 A1* | 12/2006 | Sinha | G01V 1/50 367/37 |
| 2006/0287201 A1* | 12/2006 | Georgi | G01N 24/081 507/100 |
| 2007/0150200 A1 | 6/2007 | Charara et al. | |
| 2008/0120034 A1* | 5/2008 | Georgi | G01N 24/081 702/6 |
| 2008/0175099 A1* | 7/2008 | Hawthorn | G01V 1/50 367/25 |
| 2010/0157737 A1* | 6/2010 | Miller | E21B 33/124 367/117 |
| 2011/0019500 A1 | 1/2011 | Plyushchenkov et al. | |
| 2011/0134719 A1 | 6/2011 | Kinoshita et al. | |
| 2011/0154895 A1* | 6/2011 | Charara | G01V 1/50 73/152.16 |
| 2012/0327743 A1 | 12/2012 | Parshin et al. | |
| 2015/0247942 A1* | 9/2015 | Pomerantz | G01V 1/40 702/11 |

* cited by examiner

SYSTEM AND METHOD FOR DETERMINING FLUID VISCOSITY OF A FLUID IN A ROCK FORMATION

FIELD

The present invention relates to a system and method for determining the viscosity of a fluid in a rock formation, using a Stoneley (ST) mobility and a wireline formation tester (WFT) mobility.

BACKGROUND

Reservoir fluid viscosity and permeability are two parameters that can be used for a) estimating technically recoverable and commercially developable oil and/or gas volumes, b) forecasting production, and/or c) managing oil and/or gas reservoirs. A relatively high permeability alone does not always facilitate a high flow rate from a reservoir, since fluid viscosity also has significant influence. In general, the combination of high permeability and low fluid viscosity ensure optimal flow rate.

The oil and gas industry has two main conventional methods for determining oil or gas viscosity. One method for determining oil or gas viscosity is the wireline formation tester (WFT) method. Another method for determining oil or gas viscosity is the nuclear magnetic resonance (NMR) logging method. The WFT method determines oil viscosity in the laboratory by pressure-volume-temperature (PVT) oil samples obtained by wireline formation tester, which provides a relatively accurate oil viscosity. However, the WFT method is expensive and time consuming The NMR logging method determines oil viscosity based on the NMR T2 value of oil and/or NMR porosity deficit, and provides a viscosity curve relatively soon after logging. However, the NMR method is less accurate than the WFT method, and requires that a calibration be performed based on viscosity measurements of oil samples from a wireline formation tester, i.e. using the WFT method.

The determination of reservoir fluid viscosity is often challenging even with oil samples from wireline formation tester (WFT) and NMR data. This is especially true in carbonate reservoirs.

In many cases, oil samples and/or NMR data are not available. However, at the present time, there are no methods or systems for determining a viscosity of a fluid (e.g., oil, gas, etc.) in a rock without WFT samples or NMR data.

SUMMARY

An aspect of the present invention is to provide a method of determining a viscosity of a fluid in a rock formation. The method includes determining a Stoneley mobility using a Stoneley wave measurement in a rock formation containing a fluid; determining a wireline formation tester (WFT) downhole fluid analysis (DFA) mobility by using a wireline formation tester in the rock formation; and determining a viscosity of the fluid based on the Stoneley mobility and the wireline formation tester (WFT) downhole fluid analysis (DFA) mobility.

Another aspect of the present invention is to provide a system of determining a viscosity of a fluid in a rock formation. The system includes a sonic logging tool configured to perform a Stoneley wave measurement to determine a Stoneley mobility in a rock formation containing a fluid; a wireline formation tester configured to measure varying pressure with time to determine a wireline formation tester (WFT) downhole fluid analysis (DFA) mobility in the rock formation; and a computer system configured to determine a viscosity of the fluid based on the Stoneley mobility and the wireline formation tester (WFT) downhole fluid analysis (DFA) mobility.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various Figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

In the following paragraphs, a method and system for determining oil viscosity without lab measurements of oil samples of wireline formation tester (WFT) and/or NMR data will be described in detail. According to an embodiment of the present invention, the method uses the difference between Stoneley mobility and wireline formation tester (WFT) mobility to determine oil viscosity in a rock formation or a reservoir (e.g., carbonate reservoir).

Figure 1:
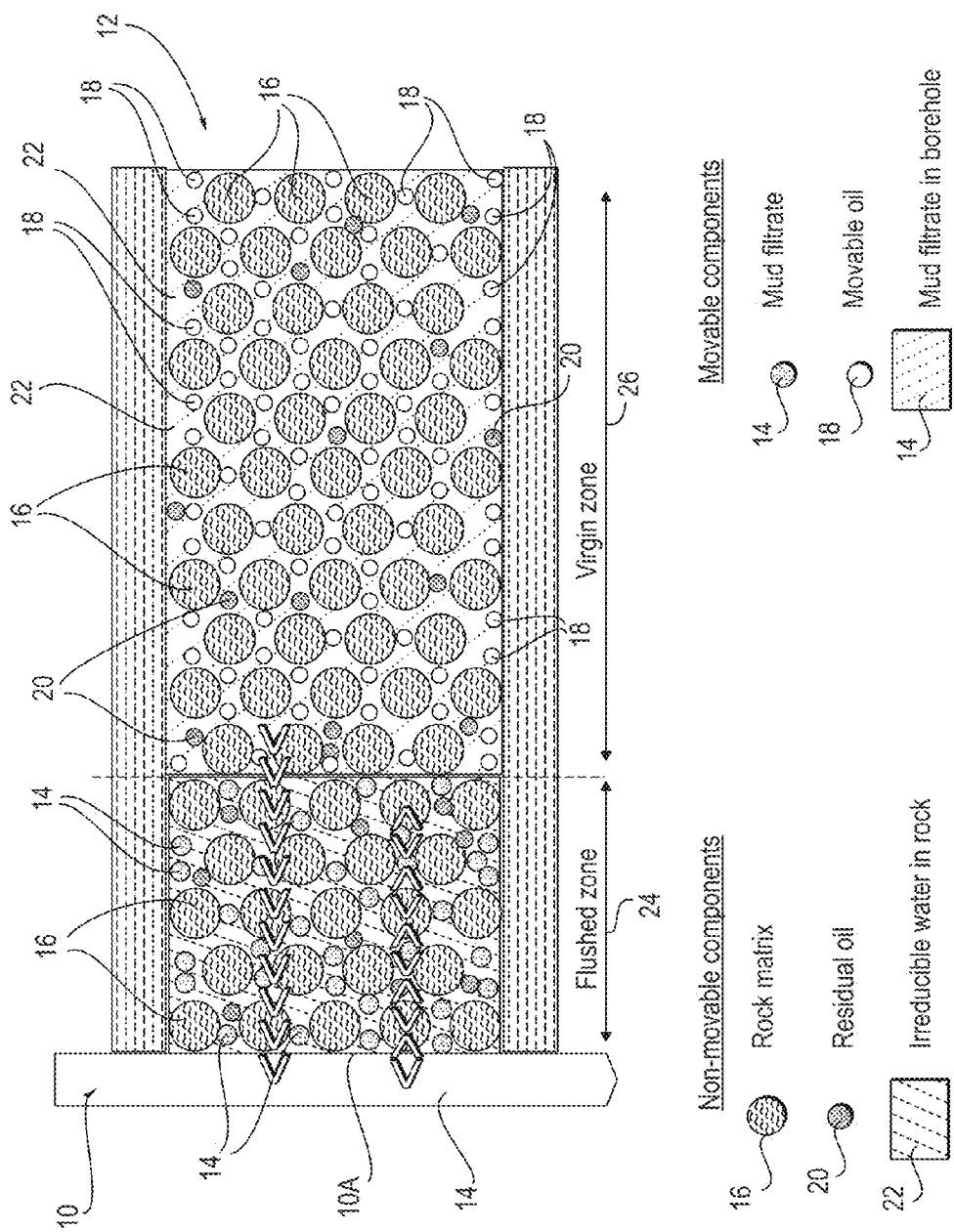
FIG. 1 depicts schematically a reservoir traversed by a borehole and the interface between the borehole and the reservoir, according to an embodiment of the present invention.

FIG. 1 depicts schematically a rock formation traversed by a borehole and the interface between the borehole and the rock formation, according to an embodiment of the present invention. As shown in FIG. 1, borehole 10 is drilled through rock formation/reservoir 12, and mud filtrate 14 is invaded into the rock formation/reservoir 12. For example, the rock formation/reservoir 12 may contain the rock matrix 16, moveable oil 18, residual oil 20 and water 22. During drilling, mud filtrate 14 is invaded into the rock formation 12. As a result, two zones 24 and 26 are created in the rock formation 12. A flushed zone 24 is the volume close to wall 10A of the borehole 10 in which all of the moveable fluids, such as moveable oil 18, are displaced by mud filtrate 14. The flushed zone 24 contains mud filtrate 14 and residual fluids 20 within rock matrix 16. The flushed zone 24 can be synonymous of an invaded zone. The virgin zone 26 on the other hand is the part of the rock formation 12 that has not been affected by the invasion of mud filtrate 14 into the rock formation 12. The virgin zone 26 contains the moveable fluids (e.g., moveable oil) 18, residual fluids (e.g., residual oil and irreducible water) 20 within rock matrix 16.

Stoneley (ST) mobility (MOBILITY_ST) of a fluid in a rock formation or reservoir is determined from the Stoneley wave which is a relatively high-amplitude surface or interface wave that typically propagates along a solid-solid or solid-liquid interface. Stoneley waves are commonly generated during borehole sonic logging with a sonic logging tool and propagate along the wall of a fluid-filled borehole. The attenuation of a Stoneley wave is sensitive to fractures and rock formation permeability. A low frequency Stoneley wave propagates as a piston-like compression of the borehole fluid. As the Stoneley wave crosses permeable zones and/or fractures, fluid movement occurs between the borehole and the rock formation. This results in energy loss (attenuation) and slowing down of the Stoneley wave.

Stoneley mobility can be derived through inversion, using Stoneley complex phase velocity equations, along with measured Stoneley waveforms which contain both Stoneley velocity and Stoneley attenuation information. In general, water viscosity is about 1 centipoise (cP). In case of water based mud, Stoneley mobility of the rock is approximately equal to the permeability of the rock matrix 16.

Stoneley mobility represents the mobility of the flowing phase of fluid in flushed zone 24 when the fluid flows through flushed zone 24. Because the viscosity of mud filtrate 14 is known, the permeability of the flushed zone 24 can be determined by Stoneley mobility and mud filtrate viscosity. In water-based mud, mud filtrate or water viscosity is approximately equal to 1 cP. Therefore, the Stoneley mobility is approximately equal to the permeability of the rock matrix 16.

Wireline formation tester (WFT) mobility (Mobility_WFT) is a function of integrated varying pressure with time. Since sending oil samples obtained from wireline formation tester (WFT) to a laboratory for analysis is expensive and time consuming, and in-situ downhole fluid sampling (DFS) is only available at a few points of a few key wells, operators often use a wireline formation tester to perform numerous pressure tests (pretests) and downhole fluid analyses (DFA). The wireline formation tester (WFT) records pressure variation with time during pretest or DFA. The wireline formation tester mobility (Mobility_WFT) is derived from the integration of varying pressure with time recorded from pretest or DFA.

In a pretest, the duration of the pretest is relatively short, and can range from a few minutes to a few tens of minutes. During pretest, most of the fluid movement relates to a small volume immediately surrounding a probe for measuring pressure, for example. The mobility derived from pretest (Mobility_WFT_PRETEST) mainly represents the mobility of the flowing phase of fluid in flushed zone 24 or the mobility of mixture of the flowing phase of fluid from both flushed zone 24 and virgin zone 26 when it flows through the flushed zone 24. In water-based mud, mud filtrate or water viscosity is approximately equal to 1 cP. Therefore, pretest mobility is approximately equal to the permeability of the rock matrix 16. However, pretest mobility may represent the mobility of the mixture of flowing phase of fluids from both flushed zone 24 and virgin zone 26.

For downhole fluid analysis (DFA), the wireline formation tester keeps pumping the fluid present in the flushed zone 24 out into the borehole 10 until the targeted formation fluid (e.g., oil) 20 from the virgin zone 26 is monitored by downhole fluid analyzers, such as electrical and/or optical sensors. The duration of a DFA is relatively long, and it usually ranges from a few minutes to a few hours. During DFA, most of the fluid movement relates to a relatively larger volume surrounding the probe.

The mobility derived from DFA (Mobility_WFT_DFA) represents the mobility of the flowing phase of fluid in virgin zone 26 (e.g., movable oil) when it flows through a completely flushed zone 24 and a small part of virgin zone 26. Therefore, the Mobility_WFT_DFA is approximately equal to the mobility of flowing phase of fluid in the virgin zone 26 (e.g., movable oil) when it flows through a completely flushed zone 24 and a small part of virgin zone 26.

As stated above, the duration of a pretest (pressure test) is relatively short. The duration of the pretest usually ranges from a few minutes to a few tens of minutes. During pretest, most of the fluid movement relates to a small volume immediately surrounding the probe. The mobility derived from pretest (Mobility_WFT_PRETEST) represents mainly the mobility of the flowing phase of fluid (e.g., oil) 18 in the flushed zone 24 or the mobility of mixture of the flowing phase of fluid (e.g., oil) 18 from both flushed zone 24 and virgin zone 26 when it flows through flushed zone 24.

In water-based mud, the viscosity of mud filtrate 14 or water is about 1 cP. Therefore, in most cases, pretest mobility (Mobility_WFT_PRETEST) is approximately equal to permeability. However, pretest mobility (Mobility_WFT_PRETEST) can also be equal to the mobility of the mixture of flowing phase of fluids (e.g., oil) 18 from both flushed zone 24 and virgin zone 26.

In the case of downhole fluid analysis (DFA), the wireline formation tester (WFA) keeps pumping fluid (e.g., water, water-based mud, etc.) in the flushed zone 24 out into borehole 10 until the targeted formation fluid (e.g., oil) 18 from the virgin zone 26 is detected and monitored by down fluid analyzers, such as electrical and/or optical sensors. The duration of a DFA is relatively long, and it usually ranges from a few minutes to a few hours. During DFA, most of the fluid movement relates to a relatively larger volume surrounding the probe. The mobility derived from DFA (Mobility_WFT_DFA) represents the mobility of the flowing phase of fluid in virgin zone (e.g., movable oil) 18 when it flows through the whole flushed zone 24 and a small part of virgin zone 26. Therefore, the mobility derived from DFA (Mobility_WFT_DFA) is approximately equal to the mobility of flowing phase of fluid (e.g, movable oil) 18 in virgin zone 26, when it flows through whole flushed zone 24 and a small part of virgin zone 26.

Therefore, wireline formation tester DFA mobility (Mobility_WFT_DFA) represents mobility of flowing phase of fluid (e.g., oil) 18 in the virgin zone 26. DFA in pay zone represents wireline formation tester DFA mobility (Mobility_WFT_DFA) of movable oil. DFA in wet zone represents wireline formation tester DFA mobility of movable water when the water flows through the flushed zone 24 mainly. A pay zone is a reservoir interval which contains oil or gas and little movable water. A wet zone is a reservoir interval which contains water and substantially no oil or gas.

The viscosity of flowing phase of fluid (e.g., oil) 18 in virgin zone 26 (Viscosity_FFVZ_DFAST, in cP units for example) is determined by the difference or ratio between DFA mobility (Mobility_WFT_DFA, in mD/cP units for example) and Stoneley mobility (Mobility_ST, in mD/cP units for example) as expressed in equation (1), for example. Although expressed herein in terms of a ratio, the term "difference" is used herein to mean either a difference between two variables or a ratio between the two variables. In the present case, the Viscosity_FFVZ_DFAST is determined using the difference (or ratio) between variables or parameters Mobility_ST and Mobility_WFT_DFA.

$$\text{Viscosity\_FFVZ\_DFAST} = \frac{\text{Mobility\_ST} * \text{Viscosity\_MF}}{\text{Mobility\_WFT\_DFA}} \quad (1)$$

where Viscosity_MF is the mud filtrate viscosity.

In pay zone, equation (1) can be used to determine movable oil viscosity. In wet zone, equation (1) can be used to determine water viscosity.

In water-based mud, equation (1) can be transformed into equation (2), as follows. Equations (1) or (2) can be used to determine movable oil viscosity of carbonate reservoir in a pay zone (i.e., a zone or a reservoir interval which contains oil or gas and little movable water).

$$\text{Viscosity\_OIL\_DFAST} = \frac{\text{Mobility\_ST} * 1.0}{\text{Mobility\_WFT\_DFA}} \quad (2)$$

In summary, the Stoneley measurement reflects an amount of mobility mainly within the flushed zone 24. During the Stoneley measurement, the dominating single phase fluid in the flushed zone 24 is mud filtrate 14. Therefore, the Stoneley measurement reflects the mobility of the mud filtrate 14 within the flushed zone 24. The wireline formation tester DFA measurement reflects the mobility within the flushed zone 24 and a small portion of the mobility of virgin zone 26. During the wireline formation tester DFA measurement, the dominating single phase fluid in the flushed zone 24 and a small portion of virgin zone 26 is the flowing phase of virgin zone oil 18 (if testing pay zone) or virgin zone water 22 (if testing wet zone).

As the Stoneley measurement and the wireline formation tester DFA measurement are both associated with a single phase fluid 18 and the flushed zone 24 of the rock formation 12, it can be considered that the flushed zone 24 includes two parts. The first part corresponds to the "effective rock matrix" which comprises the rock matrix-irreducible water 22, and the residual oil 20. The second part corresponds to the single phase fluid (mud filtrate 14 or oil 18 or rock matrix-irreducible water 22).

The Stoneley mobility measures the mobility of mud filtrate 14 flowing through the "effective rock matrix" and is related to single fluid phase flowing through the "effective rock matrix" of permeability Keff. This can be expressed mathematically by the following equation (3). The Stoneley mobility (Mobility_ST) is equal to the permeability of the effective rock matrix Keff divided by the viscosity of the mud filtrate (Viscosity_MF).

$$\text{Mobility\_ST} = \frac{K_{\textit{eff}}}{\text{Viscosity\_MF}} \quad (3)$$

The DFA mobility measures the mobility of the flowing phase of oil (e.g., movable oil) or flowing phase of water (e.g., movable water) in the virgin zone 26 flowing through mainly the "effective rock matrix" and is also related to single fluid phase flowing through the "effective rock matrix" of permeability Keff. This can be expressed mathematically by the following equation (4). The DFA mobility (Mobility_WFT_DFA) is equal to the permeability of the effective rock matrix Keff divided by the viscosity of flowing phase of fluid in the virgin zone 26 (Viscosity_FFVZ).

$$\text{Mobility\_WFT\_DFA} = \frac{K_{\textit{eff}}}{\text{Viscosity\_FFVZ}} \quad (4)$$

By dividing Mobility_ST of equation (3) by Mobility WFT DFA of equation (4), the following equation (5) can be obtained. By dividing the two equations (3) and (4), the term Keff is "eliminated" from the resulting equation (5) and thus may not be needed for the determination of the Viscosity of the flowing phase of fluid in the virgin zone 26.

$$\text{Viscosity\_FFVZ} = \frac{\text{Mobility\_ST} * \text{Viscosity\_MF}}{\text{Mobility\_WFT\_DFA}} \quad (5)$$

Equation (5) is similar to the equation (1). This shows how equation (1) can be derived from equations (3) and (4).

Figure 2:
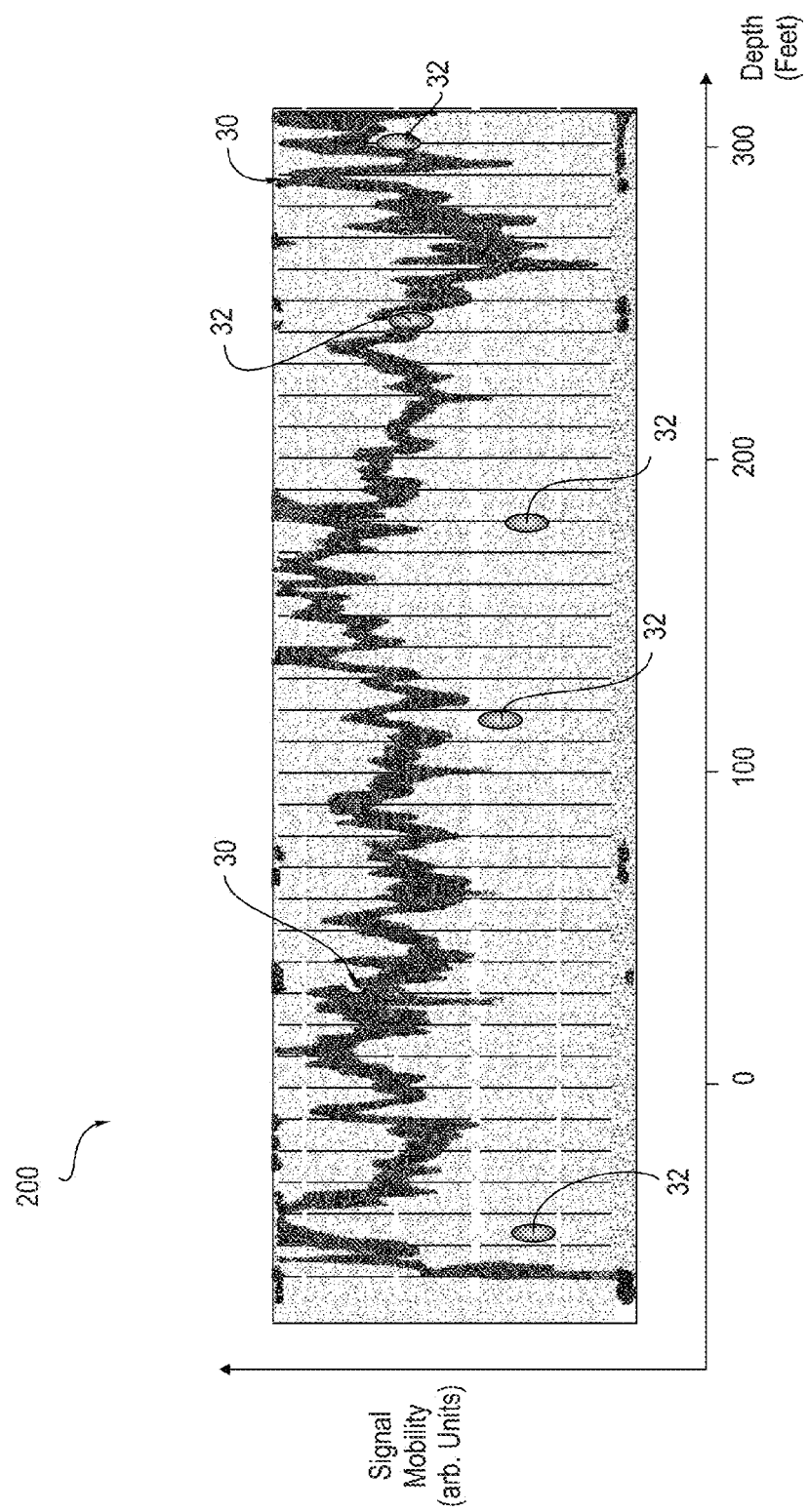
FIG. 2 shows a plot of Stonely mobility (Moblity_ST) as a function of depth and measurement points of Mobility_WFT_DFA as a function of depth, according to an embodiment of the present invention.

FIG. 2 shows a plot of the Stoneley mobility (Mobility_ST) as a function of depth, and measurements points of Mobility_WFT_DFA as a function of depth, according to an embodiment of the present invention. As shown in FIG. 2, the Stoneley mobility Mobility_ST is represented by a continuous line 30 and the DFA mobility Mobility_WFT_DFA is represented by dots 32. In wet zones, at depths greater than 200 feet in this example, Mobility_ST and Mobility_WFT_DFA overlay each other. On the other hand, in pay zones, Mobility_WFT_DFA is less than Mobility_ST. This is due to the fact that oil is more viscous than water and the Mobility_WFT_DFA takes into account oil mobility whereas Mobility_ST takes into account water mobility. The difference between these two mobility measurements can be used to calculate the oil viscosity. Table 1 shows a comparison between the oil viscosity of oil samples analyzed at laboratory and the oil viscosity determined or calculated using the equation (1), i.e., by multiplying the Stoneley mobility by the mud filtrate viscosity (which can be approximated to 1) and dividing by the modular dynamic formation tester (MDT) DFA mobility.

TABLE 1

| Depth (ft) | MDT Sample | MDT DFA Mobility (mD/cP) | MDT Oil Viscosity (cP) (By Laboratory) | Stonely Mobility (mD/cP) | Permeability from Stonely Mobility (mD) | Oil Viscosity from MDT DFA and Stoneley Mobility (cP) | Water Viscosity (cP) |
|---|---|---|---|---|---|---|---|
| 580 | Oil | 1.7 | 259 | 309 | 309 | 181.8 | 1 |
| 952 | Oil | 3 | 51.5 | 1300 | 1300 | 433.3 | 1 |
| 117 | Oil | 7.5 | 45.2 | 251 | 251 | 33.5 | 1 |
| 180 | Oil | 3.5 | 242.2 | 882 | 882 | 252.0 | 1 |
| 245 | Water | 85 | 1 | 135 | 135 | 1.6 | 1 |
| 302 | Water | 140 | 1 | 312 | 312 | 2.2 | 1 |

As shown in Table 1, the oil viscosity calculated using the method described herein approximates well the viscosity obtained in laboratory measurements. The only data point that exhibits a discrepancy between the viscosity laboratory measurement and the calculated viscosity may be due to abnormal Stoneley measurement at that point. This shows that the method of determining a viscosity of a fluid using the Stoneley mobility and the Wireline formation tester DFA mobility is a powerful tool that can be used by engineers in the field to quickly determine oil viscosity without sending the fluid sample (e.g., oil sample) to a laboratory to perform viscosity measurement which can be a lengthy process.

Figure 3:
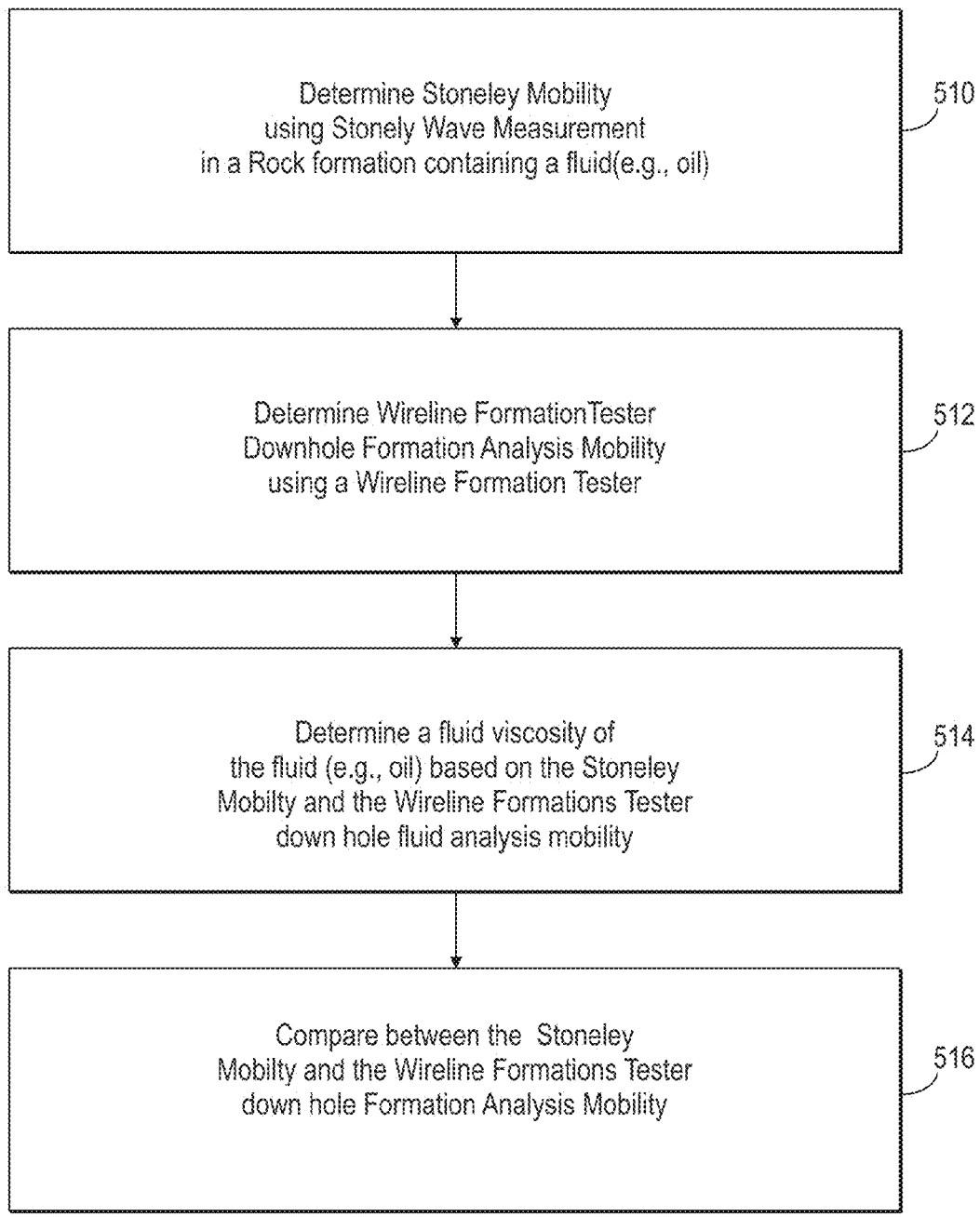
FIG. 3 depicts a flow chart of the method of determining viscosity of a fluid, according to an embodiment of the present invention.

As can be appreciated from the above paragraphs, there is provided a method of determining the viscosity of a fluid in a rock formation, according to an embodiment of the present invention. FIG. 3 depicts a flow chart of the method of determining the viscosity of the fluid, according to an embodiment of the present invention. The method includes determining a Stoneley mobility using a Stoneley wave measurement in a rock formation containing a fluid, at S10. In one embodiment, determining the Stoneley mobility using the Stoneley wave measurement includes performing the Stoneley wave measurement in the rock formation containing the fluid using a sonic logging tool. The method also includes determining a wireline formation tester (WFT) downhole fluid analysis (DFA) mobility by using a wireline formation tester in the rock formation, at S12. In one embodiment, determining the wireline formation tester (WFT) downhole fluid analysis (DFA) mobility includes deriving the wireline formation tester (WFT) downhole fluid analysis (DFA) mobility from integration of varying pressure with time recorded from the wireline formation tester (WFT). The method further includes determining the viscosity of the fluid based on the Stoneley mobility and the wireline formation tester (WFT) downhole fluid analysis (DFA) mobility, at S14.

In one embodiment, the determining of the viscosity of the fluid includes multiplying the obtained Stoneley mobility by a viscosity of mud-filtrate within the rock formation and dividing by the obtained wireline formation tester downhole fluid analysis mobility. In one embodiment, the rock formation comprises a carbonate rock formation. In one embodiment, determining the viscosity of the fluid in the rock formation comprises determining the viscosity of oil in a virgin zone (i.e., a zone essentially not having mud filtrate).

In one embodiment, the method further includes comparing between the Stoneley mobility and the wireline formation tester downhole formation analysis mobility, at S16. The method further includes differentiating pay zone (e.g., oil) from wet zone in a carbonate rock formation if there is a difference between the Stoneley mobility and the wireline formation tester downhole formation analysis mobility. Therefore, the greater the difference between the Stoneley mobility and the WFT DFA mobility, the more likely the pay zone and the wet zone are distinct. Alternatively, the smaller the difference between the Stoneley mobility and the WFT DFA mobility, the less likely (or the lesser the probability) that the pay zone can be distinguished from the wet zone.

Figure 4:
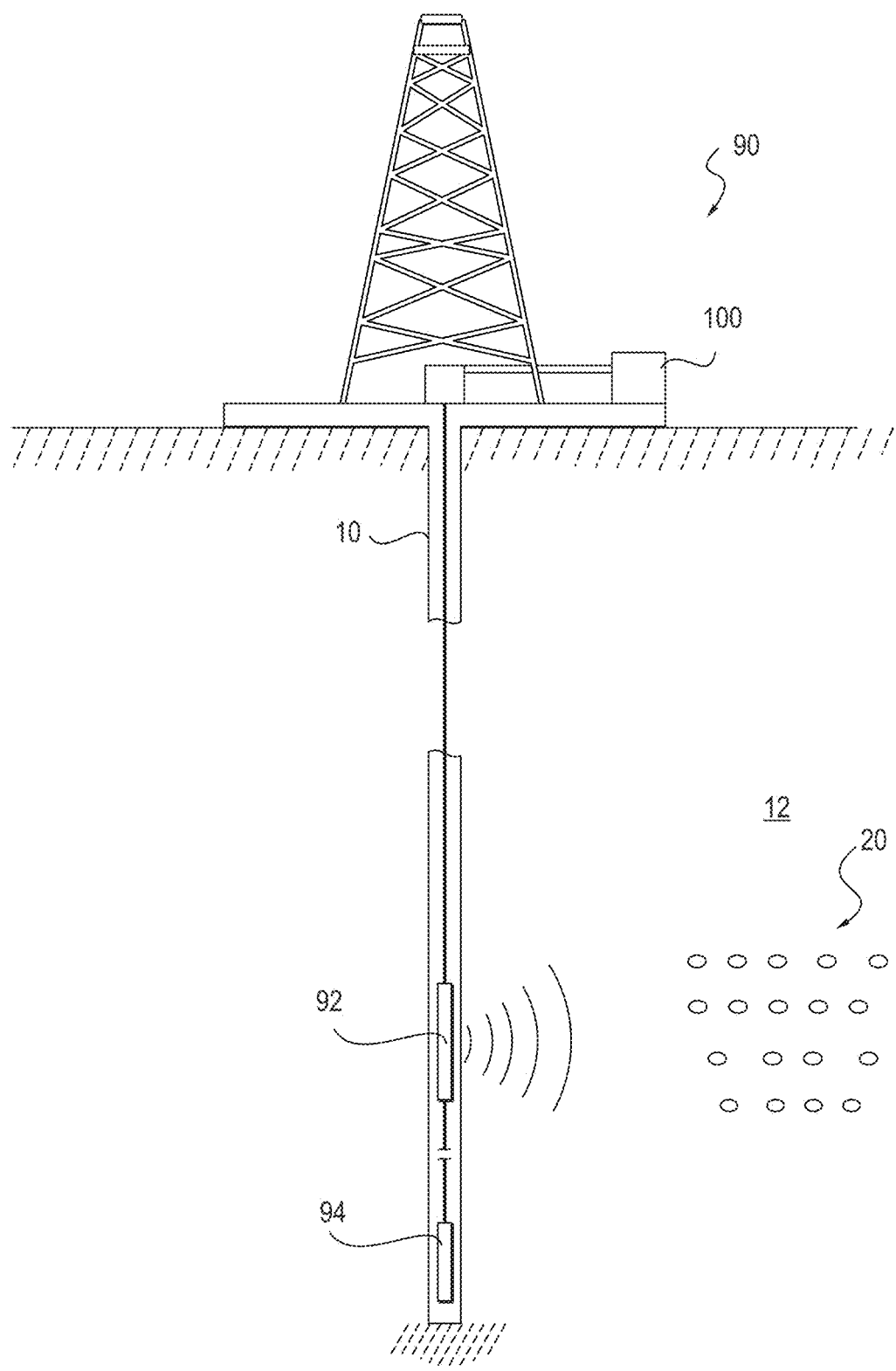
FIG. 4 depicts schematically a system of determining viscosity of a fluid in a rock formation, according to an embodiment of the present invention.

As it can be appreciate from the above paragraphs, there is also provided a system of determining a viscosity of a fluid in a rock formation, according to an embodiment of the present invention. FIG. 4 depicts schematically a system 90 for determining a viscosity of a fluid 20 in a rock formation 12. The system includes a sonic logging tool 92 configured to perform a Stoneley wave measurement to determine a Stoneley mobility in the rock formation 12 containing the fluid 20. The system further includes a wireline formation tester 94 configured to measure varying pressure with time to determine a wireline formation tester (WFT) downhole fluid analysis (DFA) mobility in the rock formation 12. The system also includes a computer system 100 configured to determine a viscosity of the fluid based on the Stoneley mobility and the wireline formation tester (WFT) downhole fluid analysis (DFA) mobility. In one embodiment, the rock formation 12 is a carbonate rock formation.

In one embodiment, the method or methods described above with respect to flowchart of FIG. 3 can be implemented as a series of instructions which can be executed by a computer, the computer having one or more processors or computer processor units (CPUs). As it can be appreciated, the term "computer" is used herein to encompass any type of computing system or device including a personal computer (e.g. a desktop computer, a laptop computer, or any other handheld computing device), or a mainframe computer (e.g. an IBM mainframe), or a supercomputer (e.g., a CRAY computer), or a plurality of networked computers in a distributed computing environment.

For example, the method(s) may be implemented as a software program application which can be stored in a computer readable medium such as hard disks, CDROMs, optical disks, DVDs, magnetic optical disks, RAMs, EPROMs, EEPROMs, magnetic or optical cards, flash cards (e.g. a USB flash card), PCMCIA memory cards, smart cards, or other media.

Alternatively, a portion or the whole software program product can be downloaded from a remote computer or server via a network such as the internet, an ATM network, a wide area network (WAN) or a local area network.

Alternatively, instead or in addition to implementing the method as computer program products) (e.g., as software products) embodied in a computer, the method can be implemented as hardware in which for example an application specific integrated circuit (ASIC) can be designed to implement the method.

Various databases can be used which may be, include, or interface to, for example, an Oracle™ relational database sold commercially by Oracle Corporation. Other databases, such as Informix™, DB2 (Database 2) or other data storage, including file-based, or query formats, platforms, or resources such as OLAP (On Line Analytical Processing), SQL (Standard Query Language), a SAN (storage area network), Microsoft Access™ or others may also be used, incorporated, or accessed. The database may comprise one or more such databases that reside in one or more physical devices and in one or more physical locations. The database may store a plurality of types of data and/or files and associated data or file descriptions, administrative information, or any other data.

Figure 5:
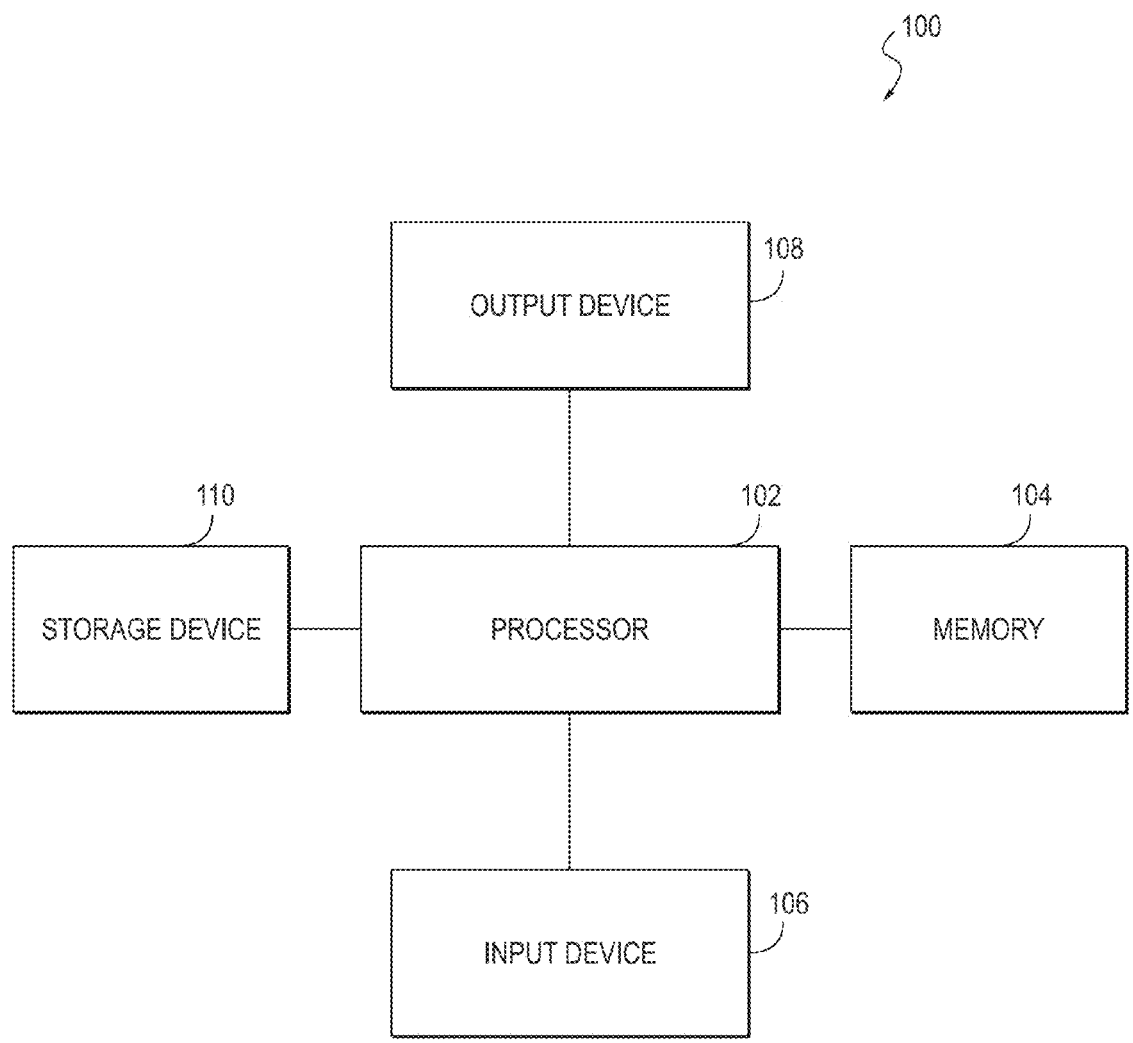
FIG. 5 is a schematic diagram representing a computer system for implementing the method, according to an embodiment of the present invention.

FIG. 5 is a schematic diagram representing a computer system 100 for implementing the methods, according to an embodiment of the present invention. As shown in FIG. 5, computer system 100 comprises a computer processor unit (e.g., one or more computer processor units) 102 and a memory 104 in communication with the processor 102. The computer system 100 may further include an input device 106 for inputting data (such as keyboard, a mouse or the like) and an output device 108 such as a display device for displaying results of the computation. The computer system 100 may further include or be in communication with a storage device 110 for storing data such as, but not limited to, a hard-drive, a network attached storage (NAS) device, a storage area network (SAN), etc. It must be appreciated that the term computer processor unit or processor is used herein to encompass one or more computer processor units. Where reference is made to a processor or computer processor unit that term should be understood to encompass any of these computing arrangements.

As it can be appreciated from the above paragraphs, the computer system 100 is configured to determine a viscosity of the fluid based on the Stoneley mobility and the wireline formation tester (WFT) downhole fluid analysis (DFA) mobility. In one embodiment, the computer system 100 includes one or more computer processor units (CPUs) 102 configured to determine the viscosity of the fluid by multiplying the obtained Stoneley mobility by a viscosity of mud-filtrate within the rock formation and dividing by the obtained wireline formation tester downhole fluid analysis mobility. In one embodiment, the one or more CPUs 102 are further configured to determine the viscosity of oil in a virgin zone. In one embodiment, the one or more CPUs 102 can also be configured to compare between the Stoneley mobility and the wireline formation tester downhole formation analysis mobility and to differentiate a pay zone from a wet zone in the rock formation 12 if there is a difference between the Stoneley mobility and the wireline formation tester downhole formation analysis mobility. In one embodiment, a greater the difference between the Stoneley mobility and the wireline formation tester downhole formation analysis mobility, the more likely the pay zone and the wet zone are distinct and a smaller the difference between the Stoneley mobility and the wireline formation tester downhole formation analysis mobility, the less likely that the pay zone is distinguished from the wet zone.

In one embodiment, the one or more CPUs 102 are configured to compare the viscosity of the fluid (e.g., oil) obtained using the Stoneley mobility and the wireline formation tester downhole fluid analysis mobility to a viscosity of the fluid (e.g., oil) obtained from a laboratory measurement.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

Furthermore, since numerous modifications and changes will readily occur to those of skill in the art, it is not desired to limit the invention to the exact construction and operation described herein. Accordingly, all suitable modifications and equivalents should be considered as falling within the spirit and scope of the invention.

What is claimed is:

1. A method of determining viscosity of a fluid in a rock formation, the method comprising:
   using a sonic logging tool to perform a Stoneley wave measurement in a rock formation containing a fluid;
   using one or more computer processor units to determine a Stoneley mobility by inversion using Stoneley complex phase velocity equations and the Stoneley wave measurement;
   using a wireline formation tester to perform downhole fluid analysis in the rock formation wherein the wireline formation tester pumps a flushed zone fluid from a flushed zone surrounding a borehole traversing the rock formation into the borehole and the wireline formation tester records pressure with time in the borehole during the downhole fluid analysis;
   using one or more computer processor units to determine a wireline formation tester (WFT) downhole fluid analysis (DFA) mobility from integration of the pressure with time recorded by the wireline formation tester; and
   using one or more computer processor units to determine a viscosity of the fluid by calculating a difference between the Stoneley mobility and the wireline formation tester (WFT) downhole fluid analysis (DFA) mobility or a ratio of the Stoneley mobility to the wireline formation tester (WFT) downhole fluid analysis (DFA) mobility.

2. The method according to claim 1, wherein the ratio of the Stoneley mobility to the wireline formation tester (WFT) downhole fluid analysis (DFA) mobility is further multiplied by a viscosity of mud-filtrate within the rock formation.

3. The method according to claim 1, wherein the rock formation comprises a carbonate rock formation.

4. The method according to claim 1, wherein the viscosity of the fluid in the rock formation is determined for oil in a virgin zone surrounding the flushed zone.

5. The method according to claim 1, further comprising comparing the Stoneley mobility and the wireline formation tester downhole formation analysis mobility and differentiating pay zone from wet zone in the rock formation if there is a difference between the Stoneley mobility and the wireline formation tester downhole formation analysis mobility.

6. The method according to claim 1, further comprising using the viscosity to estimate and forecast production of recoverable and commercially developable hydrocarbons in the rock formation.

7. The method according to claim 1, wherein the viscosity is determined without the use of lab measurements of oil samples obtained by a wireline formation tester or nuclear magnetic resonance data.

8. A system of determining a viscosity of a fluid in a rock formation, the system comprising:
   a sonic logging tool configured to perform a Stoneley wave measurement in a rock formation containing a fluid;
   a wireline formation tester configured to pump a flushed zone fluid from a flushed zone surrounding a borehole traversing the rock formation into the borehole and measure varying pressure with time in the borehole during a downhole fluid analysis; and
   a computer system comprising one or more computer processor units configured to:
   determine a Stoneley mobility by inversion using Stoneley complex phase velocity equations and the Stoneley wave measurement;
   determine a wireline formation tester (WFT) downhole fluid analysis (DFA) mobility from integration of the varying pressure with time measured by the wireline formation tester; and
   determine a viscosity of the fluid by calculating a difference between the Stoneley mobility and the wireline formation tester (WFT) downhole fluid analysis (DFA) mobility or a ratio of the Stoneley mobility to the wireline formation tester (WFT) downhole fluid analysis (DFA) mobility.

9. The system according to claim 8, wherein the ratio of the Stoneley mobility to the wireline formation tester (WFT) downhole fluid analysis (DFA) mobility is further multiplied by a viscosity of mud-filtrate within the rock formation.

10. The system according to claim 8, wherein the computer system is further configured to compare the Stoneley mobility and the wireline formation tester downhole formation analysis mobility and to differentiate a pay zone from a wet zone in the rock formation if there is a difference between the Stoneley mobility and the wireline formation tester downhole formation analysis mobility.

* * * * *